US010765315B2

United States Patent
Doushkina et al.

(10) Patent No.: US 10,765,315 B2
(45) Date of Patent: Sep. 8, 2020

(54) WIDE FIELD OF VIEW, HIGH OPTICAL POWER DISPOSABLE RETINA VIEWING SYSTEM

(71) Applicant: Novartis AG, Basel (CH)

(72) Inventors: Valentina Doushkina, Aliso Viejo, CA (US); Lingfeng Yu, Rancho Santa Margarita, CA (US)

(73) Assignee: Alcon Inc., Fribourg (CH)

( * ) Notice: Subject to any disclaimer, the term of this patent is extended or adjusted under 35 U.S.C. 154(b) by 57 days.

(21) Appl. No.: 16/012,010

(22) Filed: Jun. 19, 2018

(65) Prior Publication Data

US 2018/0368678 A1     Dec. 27, 2018

Related U.S. Application Data (60) Provisional application No. 62/522,865, filed on Jun. 21, 2017.

(51) Int. Cl.

| | |
|---|---|
| *A61B 3/13* | (2006.01) |
| *G02B 9/04* | (2006.01) |
| *G02B 13/06* | (2006.01) |
| *G02B 27/10* | (2006.01) |
| *G02B 5/18* | (2006.01) |
| *A61F 9/009* | (2006.01) |

(52) U.S. Cl.
CPC .............. *A61B 3/13* (2013.01); *A61B 3/132* (2013.01); *A61F 9/009* (2013.01); *G02B 5/1814* (2013.01); *G02B 9/04* (2013.01); *G02B 13/06* (2013.01); *G02B 27/1086* (2013.01)

(58) Field of Classification Search
CPC .......... A61B 3/13; A61B 3/132; A61F 9/009; G02B 5/1814; G02B 9/04; G02B 13/06; G02B 27/1086
USPC ......................................... 351/200, 205, 221
See application file for complete search history.

(56) References Cited

U.S. PATENT DOCUMENTS

| | | | |
|---|---|---|---|
| 7,244,026 B1 | 7/2007 | Ross, III | |
| 8,262,647 B2 | 9/2012 | Raksi | |
| 8,678,593 B2 | 3/2014 | Abt | |
| 9,402,539 B2 | 8/2016 | Buckland | |
| 9,554,702 B2 | 1/2017 | Papac | |
| 9,693,686 B2 | 7/2017 | Smith | |
| 9,724,239 B2 | 8/2017 | Yu | |
| 9,872,618 B2 | 1/2018 | Massie | |
| 2003/0214629 A1 | 11/2003 | Luloh | |
| 2005/0078910 A1 | 4/2005 | Hickingbotham | |
| 2007/0159600 A1 * | 7/2007 | Gil | A61B 3/0008 351/221 |
| 2008/0246919 A1 | 10/2008 | Smith | |

(Continued)

FOREIGN PATENT DOCUMENTS

| | | |
|---|---|---|
| EP | 1308124 A2 | 5/2003 |
| EP | 1308124 A3 | 4/2004 |

*Primary Examiner* — Tuyen Tra (57) ABSTRACT

Systems and methods for high-resolution, wide-angle viewing of a retina of an eye using an ophthalmic microscope that can view a high-resolution image of a retina formed using a wide field of view optical system. A wide field of view optical system can involve a first lens having a diffractive surface on at least one surface and a second lens housing in a shared housing. A wide field of view optical system can involve one or more lens formed from an optical grade polymer and manufactured at a cost that allows the lens to be disposable.

20 Claims, 11 Drawing Sheets

(56) References Cited

U.S. PATENT DOCUMENTS

| | | |
|---|---|---|
| 2011/0199575 A1 | 8/2011 | Buchheister |
| 2012/0242957 A1* | 9/2012 | Mordaunt |
| 2016/0089026 A1* | 3/2016 | Heeren .............. A61B 3/0025 |
| 2016/0183782 A1 | 6/2016 | Yu |
| 2017/0105620 A1 | 4/2017 | Charles |
| 2017/0188825 A1 | 7/2017 | Charles |
| 2019/0183335 A1 | 6/2019 | Yu |

* cited by examiner

WIDE FIELD OF VIEW, HIGH OPTICAL POWER DISPOSABLE RETINA VIEWING SYSTEM

BACKGROUND

Field of the Disclosure

The present disclosure relates to ophthalmic surgery, and more specifically, wide field of view, high optical power disposable retinal viewing systems.

Description of Related Art

Ophthalmic surgery is commonly performed using an operating microscope to visualize various structures in the eye. For example, during cataract surgery, the microscope if used to visualize the anterior segment of the eye such as the cornea, lens, etc. However, a standard operating microscope does not adequately view an entire posterior segment (e.g. the retina) of the eye because the natural optics of the eye (e.g. the cornea and the lens) prevent the operating microscope from focusing on features of the posterior of the eye.

To achieve superior posterior viewing during retinal surgery, an operating microscope can be used in conjunction with an additional optical system that is capable of resolving an image of the retina of the eye. For example, an ophthalmoscopic contact lens can contain an optical system for wide-angle viewing of the retina and can be placed over a patient's eye. The operating microscope can then be focused to view an image created by the contact lens. However, a contact lens system can interfere with a surgeon's ability to manipulate surgical instruments. Also, the ophthalmoscopic contact lens can become misaligned as a result of movements by the patient.

A front lens attachment can also be used in conjunction with an operating microscope to achieve wide angle viewing of the retina. A front lens attachment can include a supportive member that can hold a contact-less front lens above the eye of the patient. However, during the course of ophthalmic surgery, liquids from the eye and/or liquids used to maintain eye pressure or delivery medicine to the eye can obscure a front lens, requiring the surgeon to clean the lens or to replace the lens.

Cleaning an ophthalmoscopic contact lens and/or a front lens can be troublesome for a number of reasons. The process of cleaning the lenses can take time away from performing the surgery and cause less desirable outcomes. Also, the ophthalmoscopic contact lens and/or a front lens can have surface features (e.g. diffractive surface features) that make effective cleaning very difficult.

As an alternative to cleaning a front lens, a retinal surgeon oftentimes elects to replace the front lens with a lens from a reserve of replacement lenses to ensure continuity during surgery. However, typical lens used for wide angle retinal viewing are polished to high precision and are very expensive.

SUMMARY

The disclosed embodiments of the present technology relate to systems and methods for high-resolution, wide-angle viewing of a retina of an eye. In some embodiments, a system for high-resolution, wide-angle viewing of a retina of an eye includes an ophthalmic microscope that can view a high-resolution image of a retina formed using a wide field of view optical system. In some cases, the ophthalmic microscope is coupled with a front lens attachment configured to alternatively position a lens holder holding the wide field of view optical system into and out of a beam of light. In some embodiments, the wide field of view optical system comprises one or more lens formed from an optical grade polymer and manufactured at a cost that allows the lenses to be disposable.

Also, in some cases, a wide field of view optical system involves a first lens having a diffractive surface on at least one surface and a second lens. In these cases, the first lens and second lens can combine to form a substantially achromatic doublet. The diffractive surface can be a kinoform surface with a quadratic blaze profile. In some cases, both the first lens and the second lens are formed from optical grade polymer. In some other cases, the first lens with the diffractive surface is formed from optical grade polymer and the second lens is formed of glass. In some embodiments, a wide field of view optical system includes a single lens formed from optical grade polymer with a diffractive surface on one or more surface.

In some embodiments, a wide field of view optical system includes a shared housing that holds the first lens and the second lens. The shared housing can also couple with the lens holder of an ophthalmic microscope's front lens attachment such that, when the lens holder is positioned in the beam of light, the first lens and the second lens are positioned coaxially with the beam of light. The shared housing can include one or more geometric features for coupling with one or more of the first lens, the second lens, and the lens holder. Also, in some cases, the shared housing can be integrally formed with the first lens and/or the second lens.

In some cases, a method of high-resolution, wide-angle viewing of a retina can involve positioning a wide field of view optical system beneath a lens arrangement of an ophthalmic microscope and focusing the ophthalmic microscope to view a high-resolution image of the retina of the eye that is resolved by the wide field of view optical system.

BRIEF DESCRIPTION OF THE DRAWINGS

For a more complete understanding of the present technology, its features, and its advantages, reference is made to the following description, taken in conjunction with the accompanying drawings, in which.

DESCRIPTION

Systems and methods are disclosed for providing a wide field of view, high optical power, and disposable retinal viewing system.

Figure 1:
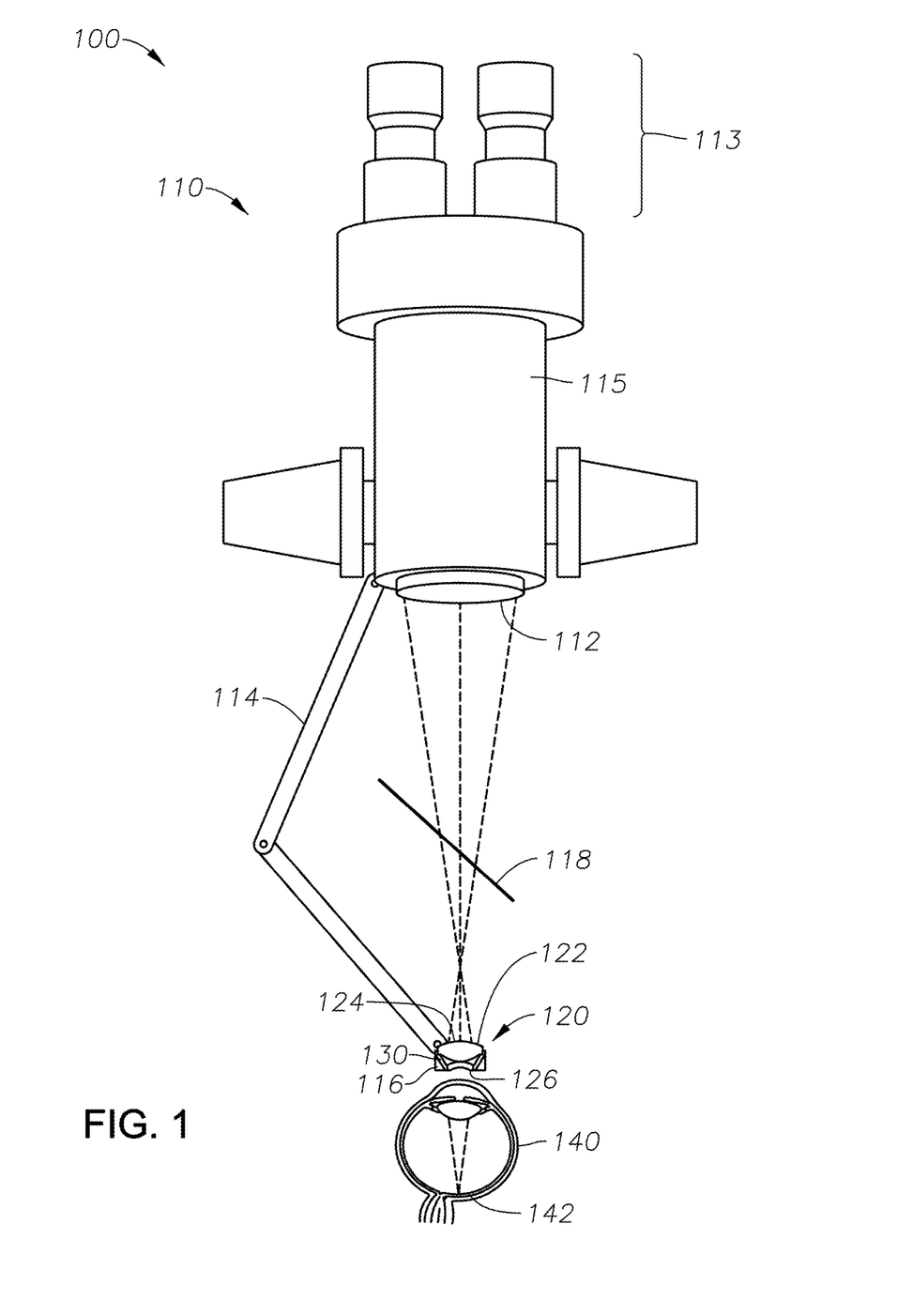
FIG. 1 illustrates a system for high resolution, wide field of view viewing of the retina of an eye.

FIG. 1 illustrates a system 100 for high resolution, wide field of view viewing of the retina 142 of an eye 140. The system 100 can include a wide field of view optical system 120 used in conjunction with an ophthalmic microscope 110. The ophthalmic microscope 110 can include a housing 115 containing a lens arrangement including an objective lens 112. The ophthalmic microscope 110 also includes a binocular eyepiece arrangement 113 for viewing images formed from a beam of light reflected from the eye 140. The system 100 can also include a beamsplitter 118 to redirect a portion of the beam of light.

The wide field of view optical system 120 can include a first lens 122 with a diffractive surface 124 and a second lens 126. The first lens 122 and the second lens 126 can be coupled together within a shared housing 130.

The system 100 can also include a front lens attachment 114 coupled with the ophthalmic microscope 110. The front lens attachment can include a lens holder 116 which can couple with the shared housing 130. In some cases, the front lens attachment 114 can be jointed and can articulate in order to alternatively position the lens holder 116 and the shared housing 130 into and out of the beam of light. In some cases, the front lens attachment 114 is configured as a screw drive that can move the lens holder 116 up and down and the lens holder is configured to rotate into and out of the beam of light.

In some cases, the lens arrangement of the ophthalmic microscope 110 is generally selected to resolve an image of the anterior (not labeled) of an eye. Similarly, the combined prescription of the first lens 122 and the second lens 126 can selected to resolve an image of the retina 142 of the eye 140 when used in combination with the lens arrangement of the ophthalmic microscope 110. In these cases, an ophthalmic professional can alternatively view the anterior and retina 142 of the eye 140 by articulating the lens holder 116 and the shared housing 130 into and out of the beam of light.

Figure 2:
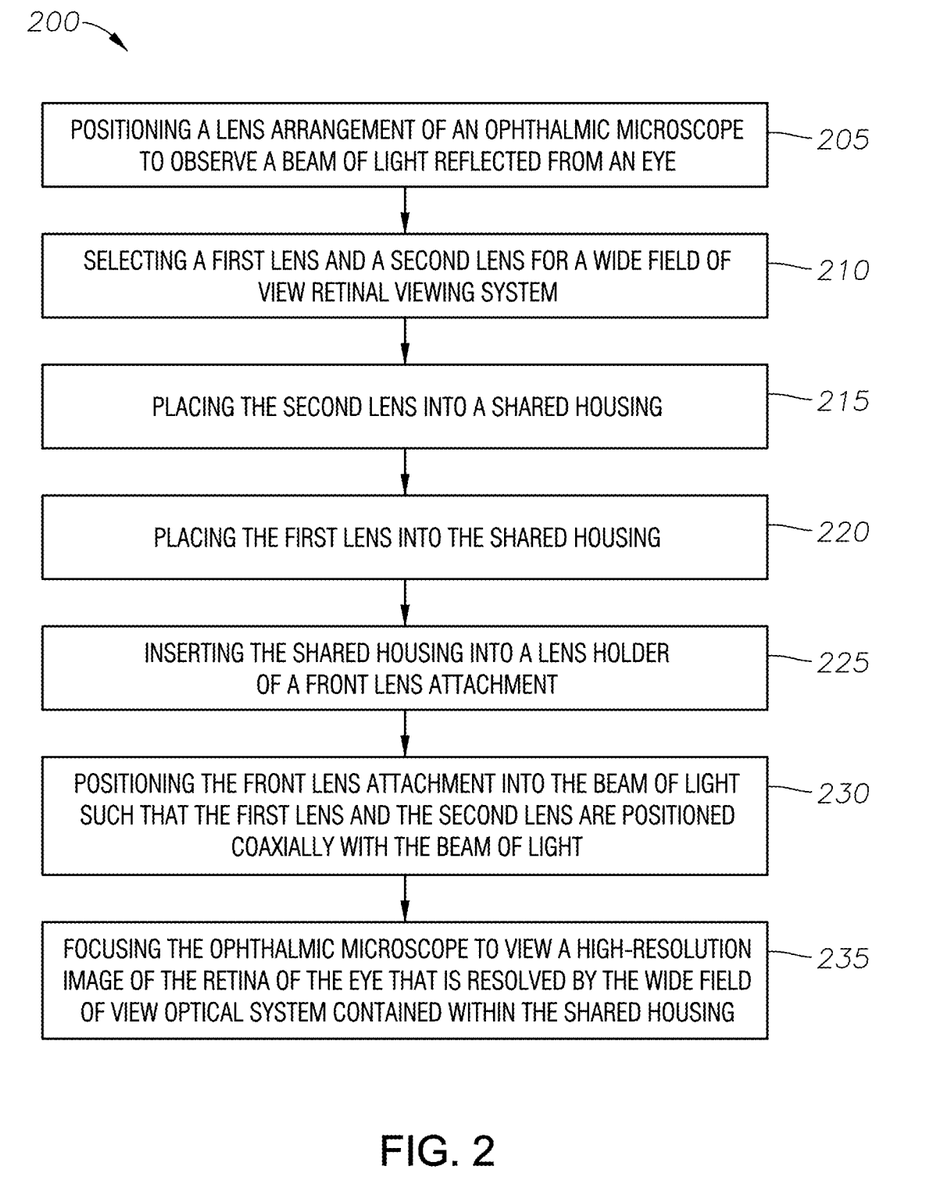
FIG. 2 illustrates a method of high-resolution, wide-angle viewing of a retina.

FIG. 2 illustrates a method 200 of high-resolution, wide-angle viewing of a retina. The method 200 involves positioning a lens arrangement of an ophthalmic microscope to observe a beam of light reflected from an eye 205 and selecting a first lens and a second lens for a wide field of view retinal viewing system 210. The first lens can be a polymer lens with a first side having a convex surface and a second side having a diffractive surface profile. In some cases, both the first side and the second side of the first lens have a diffractive surface profile. The second lens can include a glass or polymer lens having smooth surface profiles and at least one concave surface. The first lens and the second lens can combine to form a substantially achromatic doublet.

Next, the method 200 involves placing the second lens into a shared housing with a concave surface of the second lens facing an open bottom of the shared housing 215. In some cases, a bottom internal shelf of the shared housing supports the second lens, as described in more detail below. Also, the method 200 involves placing the first lens into the shared housing with a convex surface of the first lens facing the open bottom of the shared housing and with a diffractive surface of the first lens facing an open top of the shared housing 220.

After the first lens and the second lens are housed within the shared housing, the method 200 involves inserting the shared housing into a lens holder of a front lens attachment coupled with the ophthalmic microscope 225 with the open bottom of the shared housing facing the eye and with the open top of the shared housing facing the ophthalmic microscope.

Next, the method 200 involves positioning the front lens attachment into the beam of light such that the first lens and the second lens are positioned coaxially with the beam of light 230 and focusing the ophthalmic microscope to view a high-resolution image of the retina of the eye that is resolved by the wide field of view optical system contained within the shared housing 235.

Figure 3A:
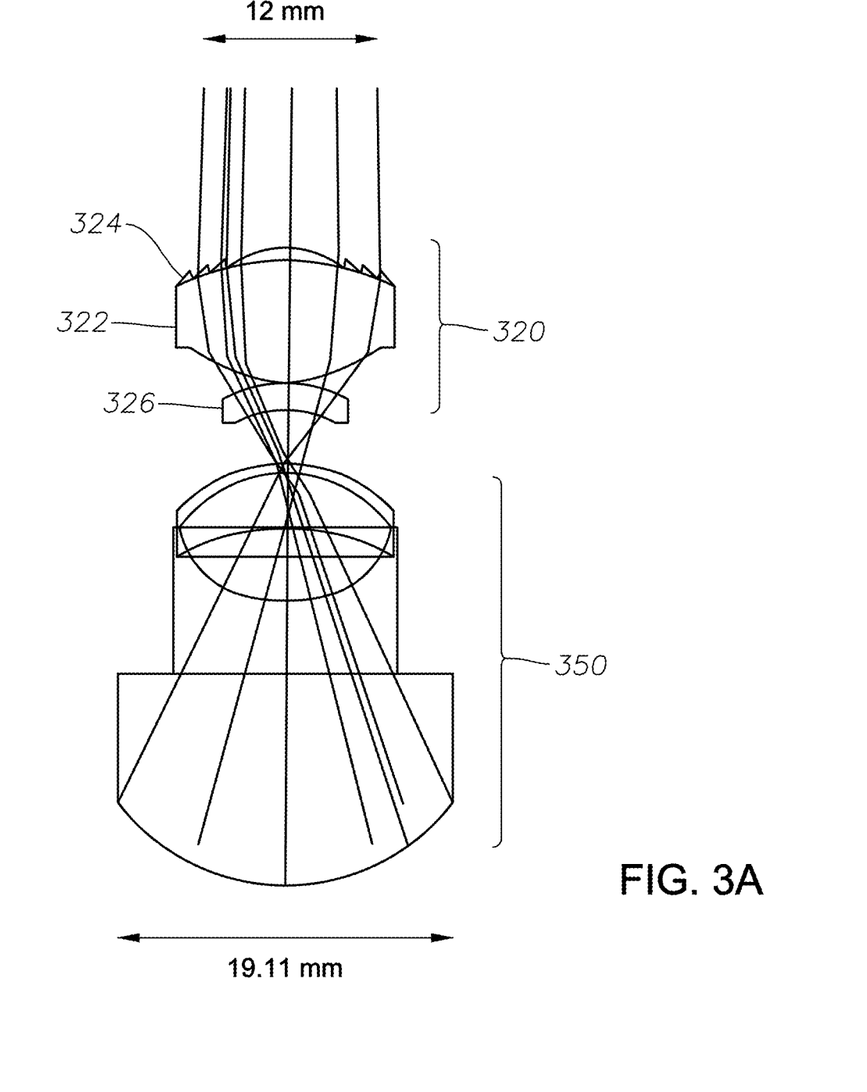
FIG. 3A illustrates an example of a wide field of view optical system resolving light from a model of a human eye.
Figure 3B:
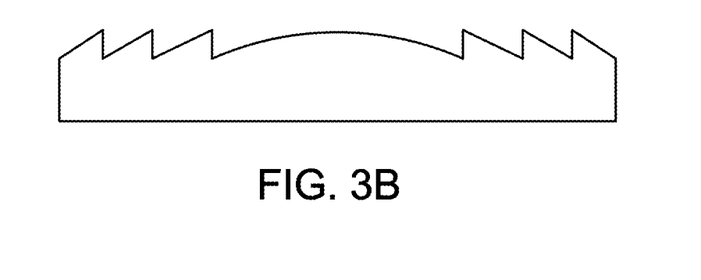
FIG. 3B illustrates an example of a diffractive kinoform surface having a quadratic blaze profile.

FIG. 3A illustrates an example of a wide field of view optical system 320 resolving light from a model 350 of a human eye according to some embodiments of the present disclosure. The wide field of view optical system 320 includes a first lens 322 and a second lens 326. The first lens 322 can be a converging lens and can include a diffractive surface 324 on at least one surface. The diffractive surface 324 increases the optical power of the wide field of view optical system 320 and creates, along with the second lens 326, a substantially achromatic doublet. FIG. 3B illustrates an example of a diffractive kinoform surface having a quadratic blaze profile according to some embodiments of the disclosed technology. In some cases, an additional protective layer of polymer or glass can be applied to a diffractive surface.

In some cases, one or more of the first lens 322 and the second lens 326 of the wide field of view optical system 320 comprise an optical grade polymer selected for high optical performance and wide field of view optics. Further, optical grade polymer can allow the wide field of view optical system 320 to be made with a low manufacturing cost at high production value to allow for disposable use. Using a wide field of view optical system 320 having a production cost low enough to be disposable can allow a surgeon to quickly and simply dispose and replace lens without significantly increasing the cost of the surgery, e.g. during the course of ophthalmic surgery when liquids from the eye and/or liquids used to maintain eye pressure or delivery medicine to the eye obscure a lens in the wide field of view optical system 320.

As mentioned above, the wide field of view optical system 320 can include one or more optical surfaces such as refractive, reflective, and diffractive substrates with spherical, aspherical, cylindrical, and freeform prescriptions. Forming these surfaces with optical glass is achieved using a time-consuming high precision optical polishing and/or magneto rheological finishing (MRF) methods and is extremely expense. Optical grade polymer is conducive for allowing these optical surfaces to be manufactured at a low enough cost for the wide field of view optical system 320 to be disposable since only a prototype needs to be formed by a single point diamond turning (SPDT) method and subsequent copies can be made using injection molding, compression molding, etc.

Figure 4A:
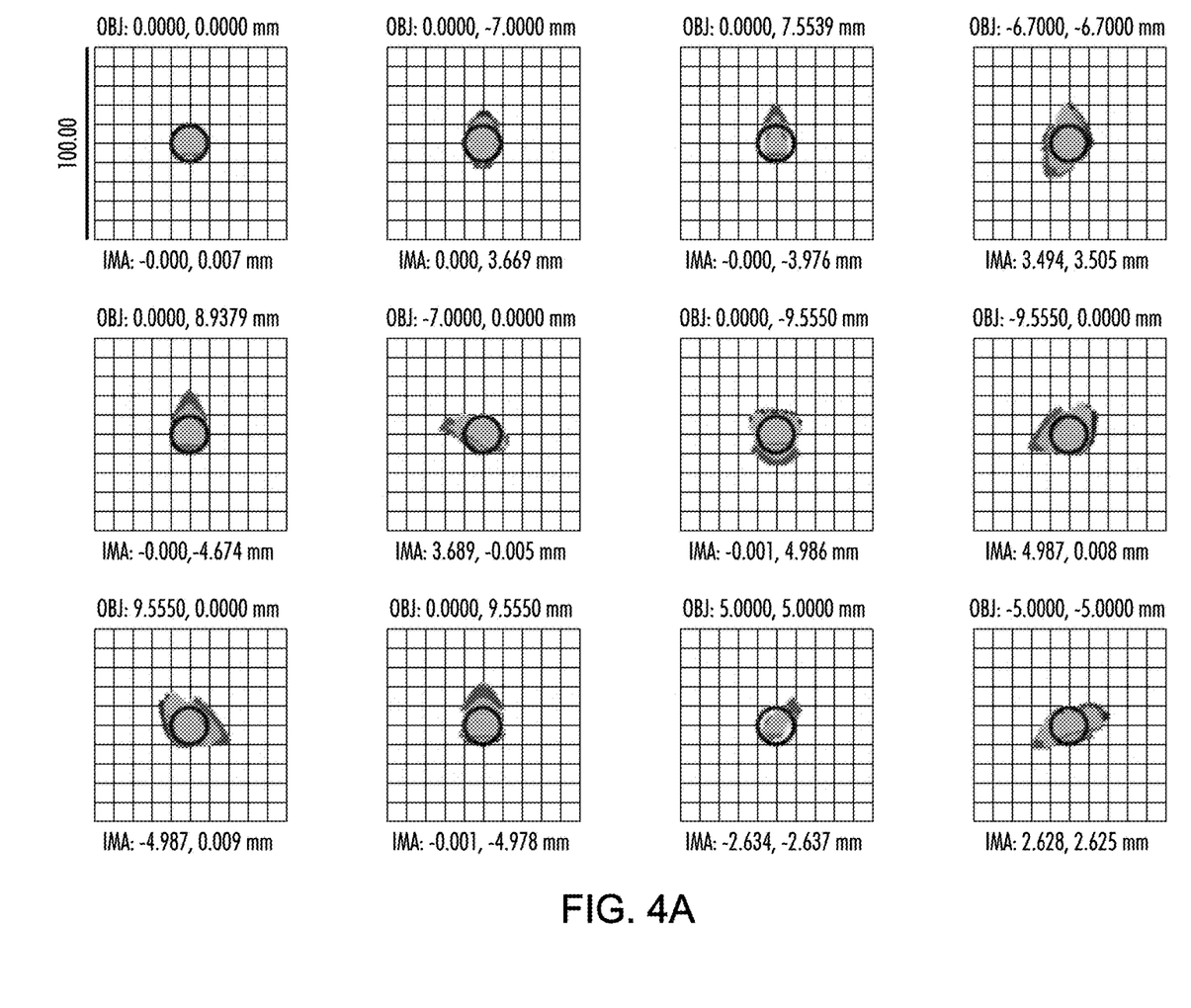
FIG. 4A illustrates quantified results of an eye model image spot size formed in intermediate plane using the stand-alone wide field of view optical system described in FIG. 3A.
Figure 4B:
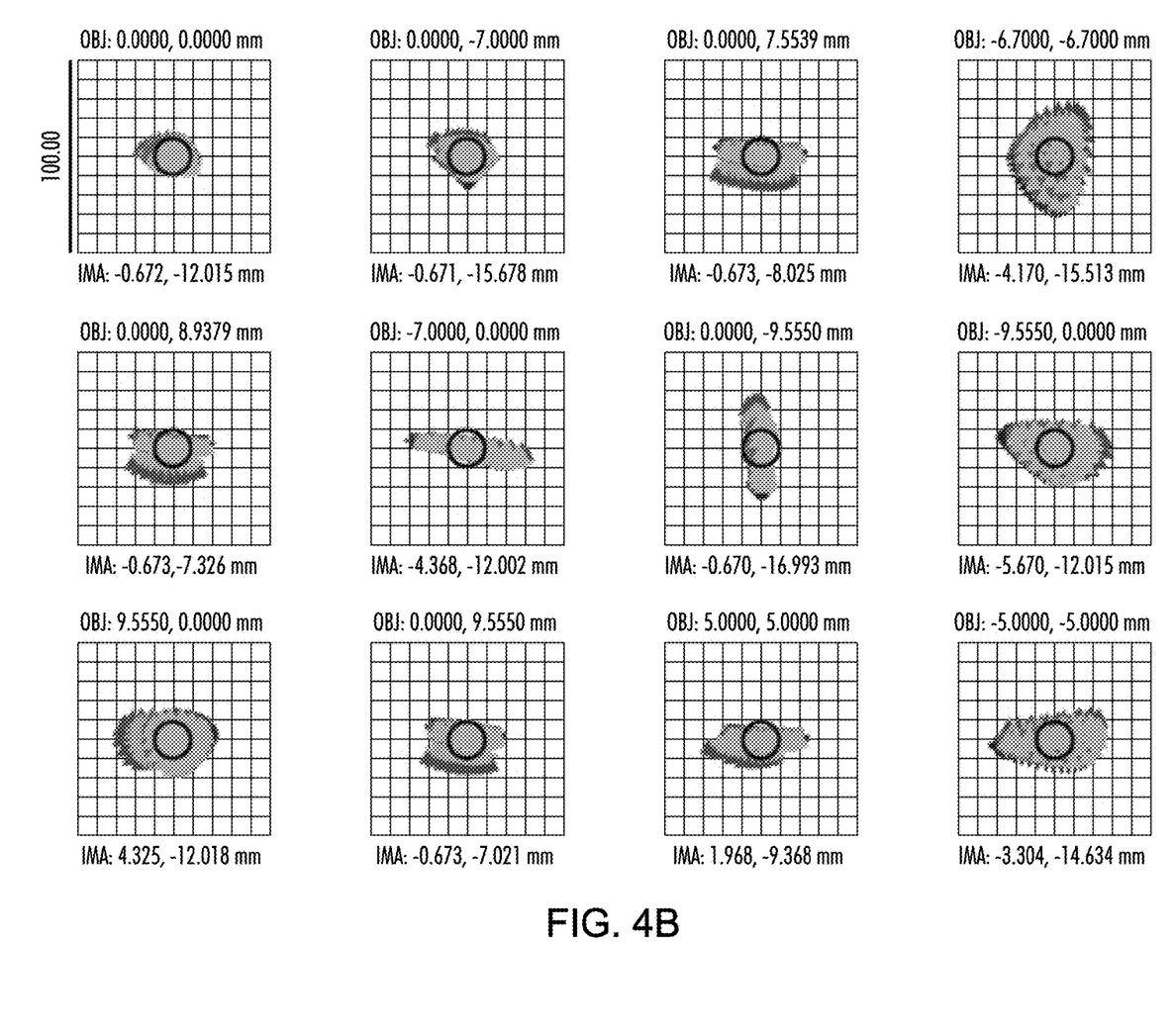
FIG. 4B illustrates quantified results of an eye model image spot size formed in intermediate plane using the wide field of view optical system described in FIG. 3A integrated with an ophthalmic microscope.
Figure 4C:
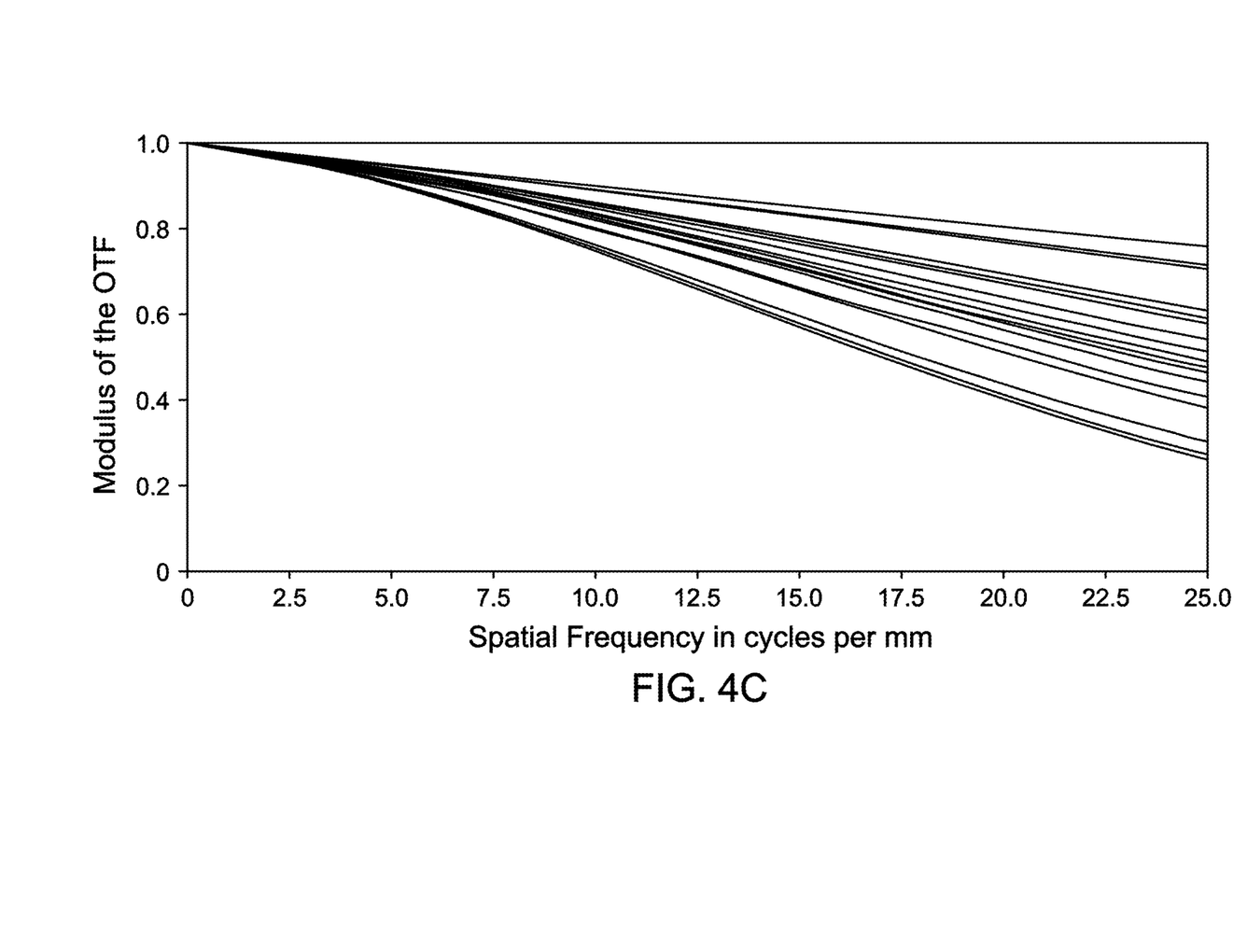
FIG. 4C illustrates quantified results of Modulation Transfer Function of the wide field of view optical system described in FIG. 3A integrated with the microscope model.

The inventor has observed a wide field of view optical system 320 formed from an optical grade polymer perform extremely well in spot size and Modulation Transfer Function testing. FIG. 4A illustrates quantified results of an eye model image spot size formed in intermediate plane using the stand-alone wide field of view optical system described in FIG. 3A. FIG. 4B illustrates quantified results of an eye model image spot size formed in intermediate plane using the wide field of view optical system described in FIG. 3A integrated with an ophthalmic microscope. FIG. 4C illustrates quantified results of Modulation Transfer Function of the wide field of view optical system described in FIG. 3A integrated with the microscope model. The MTF offers diffraction limited resolution in the center area of retina degrading on the periphery to about thirty percent.

Referring again to FIG. 3A, the first lens 322 and the second lens 326 can combine to produce an optical power of at least one-hundred twenty-eight diopter. Also, the first lens 322 and the second lens 326 can resolve, in combination with an ophthalmic microscope, an image of the retina of an eye at a resolution of at least ten microns in the center of the retina and twenty microns on the periphery of the retina at wide angles of view over at least a diameter of 19.11 millimeters.

In some cases, an optical polymer can be selected that is both capable of being manufactured at a low cost and sterilizable for multiple uses. For example, a wide field of view optical system 320 made with polyetherimide (PEI) can achieve similar results to those illustrated in FIGS. 4A-4C and can withstand various sterilization methods including ethylene oxide sterilization, gamma radiation, autoclaving, dry heat sterilization, etc.

In some cases, a first lens in a wide field of view optical system can be a disposable optical grade polymer while a second lens comprises a traditional glass lens. As explained above, a first lens can include a diffractive surface which can be obscured in the present of liquid and which can be especially difficult to remove liquid from. However, the second lens can have a smooth surface and therefore easier to wipe clean, thus allowing a glass lens to be used, sterilized, and re-used.

As explained above, the first and second lenses in a wide field of view optical system can be arranged in a shared housing. In some cases, one or both the first and the second lenses are pre-assembled or integrally formed within a shared housing. In some other cases, a shared housing contains geometric feature for coupling with one or both of the first and second lenses.

Figure 5A:
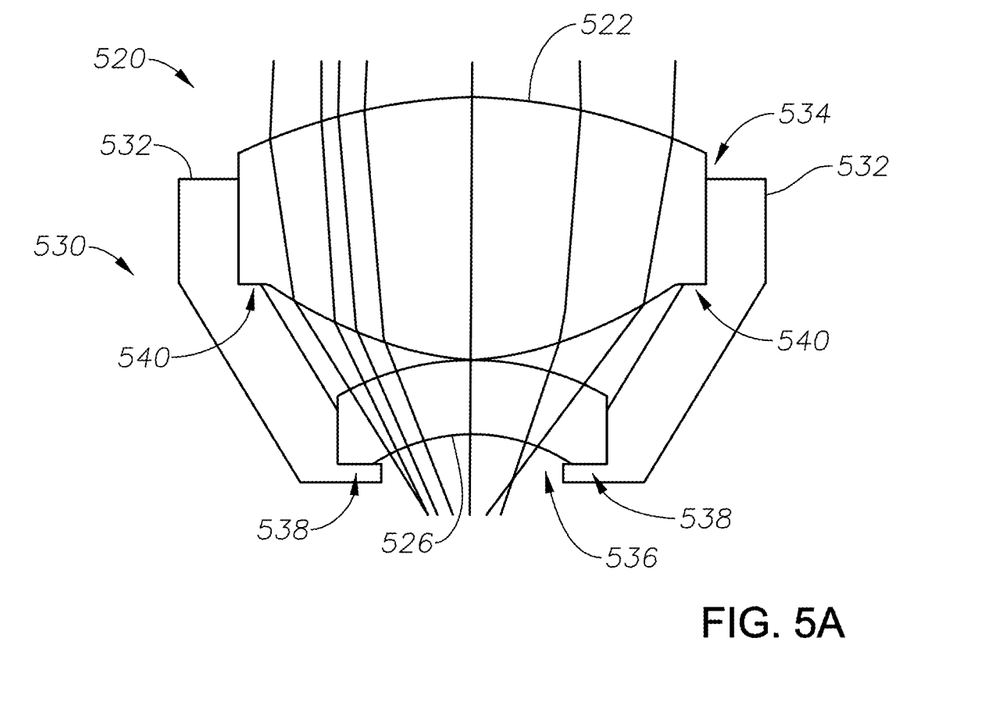
FIG. 5A illustrates a side view cross section of a shared housing for the first lens and the second lens of a wide field of view optical system.

FIG. 5A illustrates a cross section of the side view of a shared housing 530 for a first lens 522 and a second lens 526 of a wide field of view optical system 520. The surface 532 of the shared housing 530 can extend around the center vertical axis such that the shared housing 530 is bowl-shaped with an open top 534 and open bottom 536. Also, a bottom internal shelf 538 near the open bottom 536 is configured to support the second lens 526 and a top internal shelf 540 near the open top 534 is configured to support the first lens 522. Like the wide field of view optical system 520, the shared housing 530 can be manufactured (e.g. using compression molding, injection molding, etc.) at a cost low enough to allow the shared housing 530 to be disposable.

In some cases, the surface 532 of the shared housing 530 can be a rigid material (e.g. aluminum, rigid plastic, etc.) that can be injection molded, for example. In these cases, the first lens 522 and the second lens 526 can float in or click into the shared housing 530. In some cases, the surface 532 of the shared housing 530 can be formed from an at least somewhat elastic material. In these cases, the surface 532 of the shared housing around the top internal shelf 540 and/or the bottom internal shelf 538 can be slightly smaller than the dimensions of the first lens 522 and second lens 526, respectively. The smaller dimensions can allow the first lens 522 and second lens 526 to stretch the elastic surface 532 of the shared housing 530 and become held within the shared housing 530 by the restoring force of the elastic surface 532. Also, the elastic surface 532 can ensure proper axial alignment of the first lens 522 and the second lens 526.

Figure 5B:
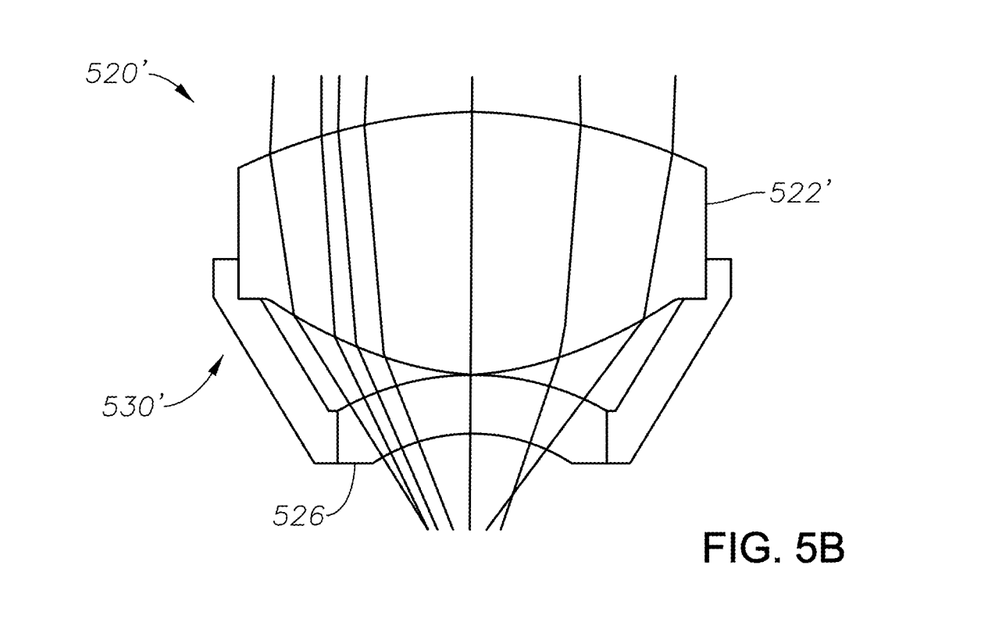
FIG. 5B illustrates a side view cross section of a shared housing integral with the second lens and the first lens of a wide field of view optical system snapped or placed within the shared housing.

Another advantage of using optical polymers is the integration of optical and mechanical functionalities, thus simplifying assembly of and alignment a wide field of view optical system 520 by reducing the number of components. For example, in some cases, the second lens 526 can integrated with the shared housing 530 as one part. FIG. 5B illustrates the cross section of a side view of a shared housing 530' integral with a second lens 526' and a first lens 522' of a wide field of view optical system 520' snapped or placed within the shared housing 530'.

Figure 6:
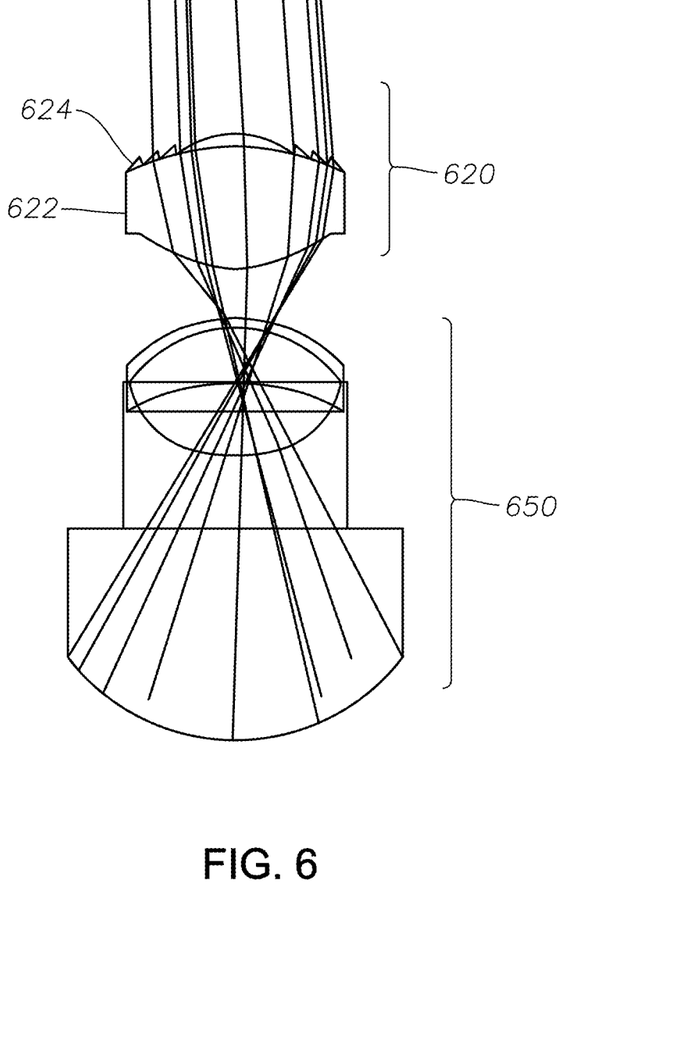
FIG. 6 illustrates an example of a wide field of view optical system resolving light from a model of a human eye.
Figure 7A:
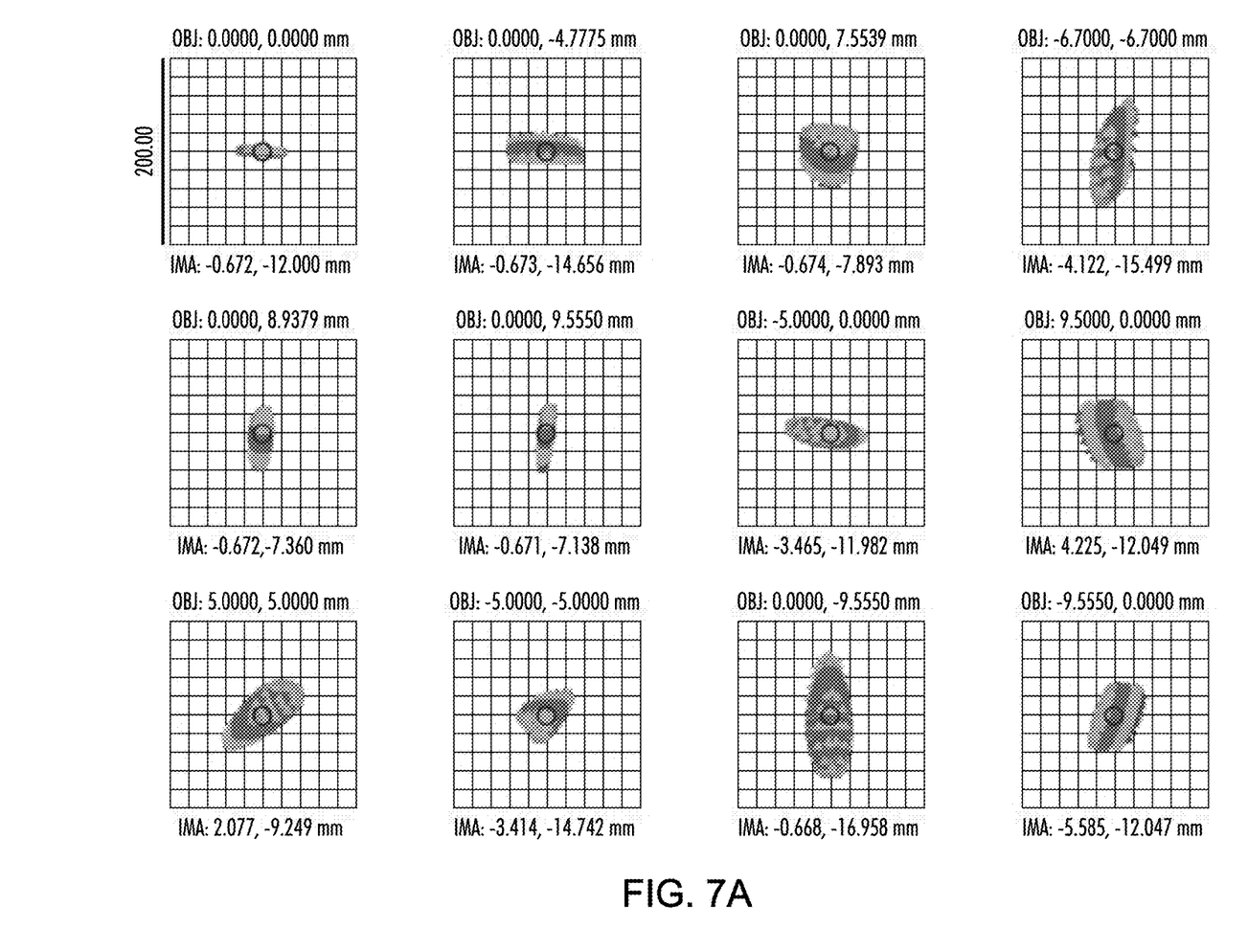
FIG. 7A illustrates quantified results of an eye model image spot size formed in intermediate plane using a single, refractive/diffractive hybrid lens in the wide field of view optical system described in FIG. 6 integrated with an ophthalmic microscope.
Figure 7B:
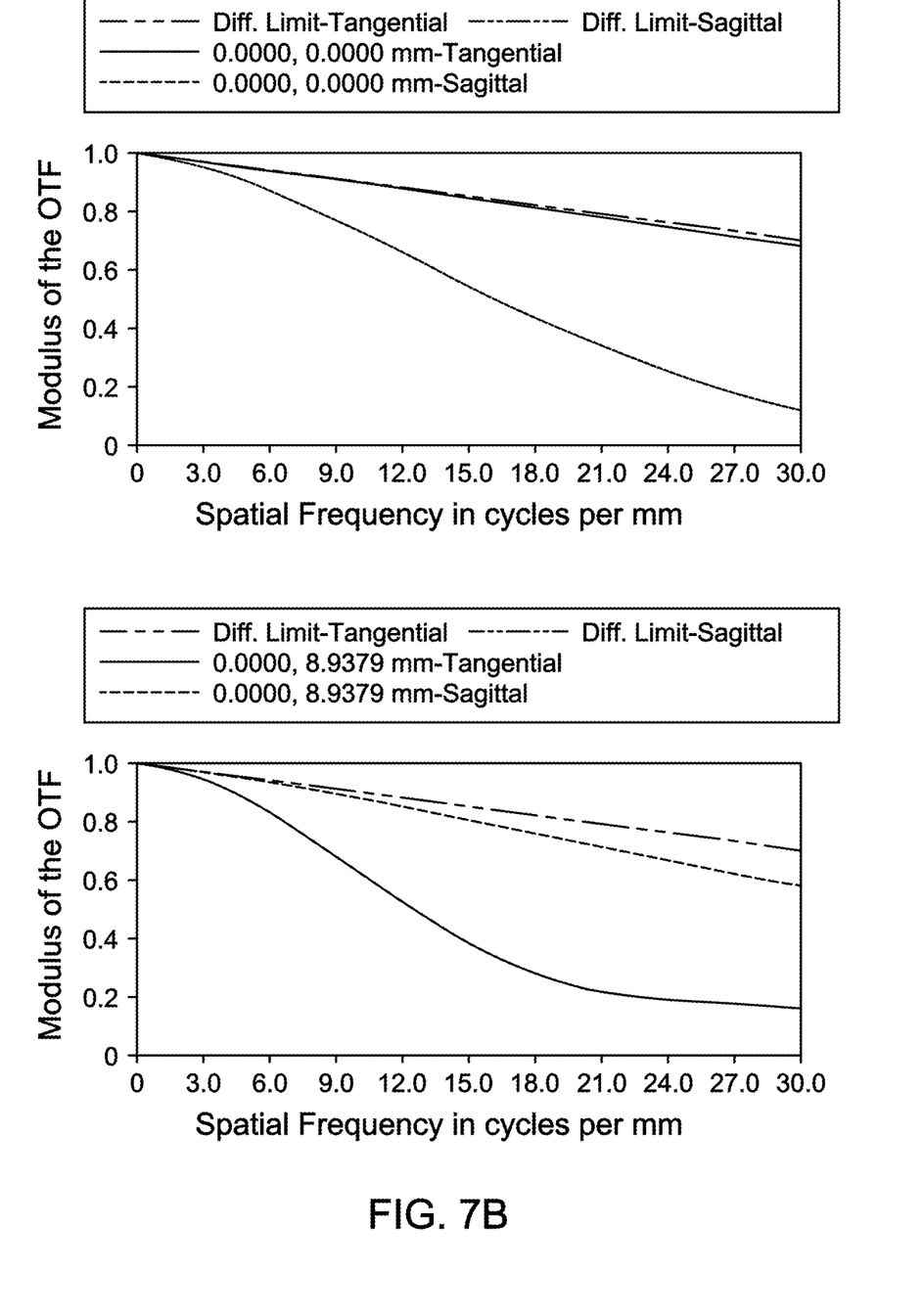
FIG. 7B illustrates quantified results of Modulation Transfer Function of a single, refractive/diffractive hybrid lens in the wide field of view optical system described in FIG. 6 integrated with the ophthalmic microscope.

Although the description above refers to a wide field of view optical system including a pair of lens, some embodiments also involve a single disposable optical grade polymer lens with a comparable optical power and which can resolve, in combination with an ophthalmic microscope, an image of the retina of an eye at comparably high resolutions. FIG. 6 illustrates an example of a wide field of view optical system 620 resolving light from a model 650 of a human eye according to some embodiments of the present disclosure. The wide field of view optical system 620 includes a single lens 622 that is a refractive/diffractive hybrid. The single lens 622 includes a diffractive surface 624, e.g. a diffractive kinoform surface having a quadratic blaze profile. Like the multi-lens solutions described above, the inventor has observed a wide field of view optical system 620 with a single refractive/diffractive hybrid lens formed from an optical grade polymer perform extremely well in spot size and Modulation Transfer Function testing. FIG. 7A illustrates quantified results of an eye model image spot size formed in intermediate plane using the single, refractive/diffractive hybrid lens in a wide field of view optical system described in FIG. 6 integrated with an ophthalmic microscope. FIG. 7B illustrates quantified results of Modulation Transfer Function of a single, refractive/diffractive hybrid lens in the wide field of view optical system described in FIG. 6 integrated with the ophthalmic microscope.

In some cases, a single, refractive/diffractive hybrid lens can be enhanced by forming a diffractive kinoform surface on both lens surfaces. In these cases, a window can be placed between the single, refractive/diffractive hybrid lens and the patient's eye to prevent fluids from contaminating the optics.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A system for high-resolution, wide-angle viewing of a retina comprising:
   an ophthalmic microscope having a lens arrangement for viewing images formed from a beam of light reflected from an eye;
   a front lens attachment configured to alternatively position a lens holder into and out of the beam of light;
   a wide field of view optical system including:
      a first lens having a diffractive surface on at least one surface of the first lens;
      a second lens, wherein the first lens and second lens combine to form a substantially achromatic doublet; and
      a shared housing configured to house the first lens and the second lens and configured to couple with the lens holder such that, when the lens holder is positioned in the beam of light, the first lens and the second lens are positioned coaxially with the beam of light and allow the ophthalmic microscope to view a high-resolution image of the retina of the eye.

2. The system of claim 1, further comprising:
   a beam splitter located in the beam of light between the lens arrangement of the ophthalmic microscope and the front lens attachment.

3. The system of claim 1, wherein the wide field of view optical system has an optical power substantially equal to 128 diopter.

4. The system of claim 1, wherein the ophthalmic microscope and the wide field of view optical system resolve the retina of the eye at least at 10 microns (μm) at a center of the retina and at least at 20 μm on a periphery of the retina at angles of view over at least a diameter of 19.11 millimeters.

5. The system of claim 1, wherein the first lens comprises a converging lens formed from a polymer by a molding process.

6. The system of claim 5, wherein the polymer comprises polyetherimide.

7. The system of claim 1, wherein the diffractive surface of the first lens comprises a kinoform surface with a quadratic blaze profile.

8. The system of claim 1, wherein the second lens comprises a polymer lens formed by a molding process.

9. The system of claim 1, wherein the second lens comprises a glass lens without a diffractive surface, thereby allowing liquid that comes into contact with the second lens to be removed without affecting an optical prescription of the lens.

10. The system of claim 1, wherein the shared housing includes a first geometric profile for coupling with the first lens and a second geometric profile for coupling with the second lens.

11. The system of claim 1, wherein the shared housing is integrally formed with the second lens and the shared housing includes a geometric profile for coupling with the first lens.

12. A method of high-resolution, wide-angle viewing of a retina comprising:
   positioning a lens arrangement of an ophthalmic microscope to observe a beam of light reflected from an eye;
   coupling a wide field of view optical system with a front lens attachment that is configured to alternatively position the wide field of view optical system into and out of the beam of light, the wide field of view optical system including:
      a first lens having a diffractive surface on at least one surface of the first lens;
      a second lens, wherein the first lens and second lens combine to form a substantially achromatic doublet; and
      a shared housing containing the first lens and the second lens;
   articulating the front lens attachment to position the shared housing into the beam of light, such that the first lens and the second lens are positioned coaxially with the beam of light;
   focusing the ophthalmic microscope to view a high-resolution image of the retina of the eye that is resolved by the wide field of view optical system.

13. The method of claim 12, wherein coupling the wide field of view optical system with the front lens attachment further comprises:
   placing the second lens into the shared housing with a concave surface of the second lens facing an open bottom of the shared housing;
   placing the first lens into the shared housing with a convex surface of the first lens facing the open bottom of the shared housing and with the diffractive surface of the first lens facing an open top of the shared housing; and
   inserting the shared housing into a lens holder of the front lens attachment with the open bottom of the shared housing facing the eye and with the open top of the shared housing facing the ophthalmic microscope.

14. The method of claim 12, further comprising:
   articulating the front lens attachment to position the shared housing out of the beam of light; and
   focusing the ophthalmic microscope to view an image of the anterior of the eye.

15. A lens apparatus comprising:
   a first lens having a diffractive surface on at least one surface of the first lens;
   a second lens, wherein the first lens and second lens combine to form a wide field of view optical system that is a substantially achromatic doublet; and
   a shared housing configured to house the wide field of view optical system, such that the first lens and the second lens are coaxially aligned when placed in a beam of light of an ophthalmic microscope, thereby allowing the ophthalmic microscope to view a high-resolution image of a retina of an eye.

16. The lens apparatus of claim 15, wherein the wide field of view optical system has an optical power substantially equal to 128 diopter.

17. The lens apparatus of claim 15, wherein the ophthalmic microscope and the wide field of view optical system resolve the retina of the eye at least at 10 microns (μm) at a center of the retina and at least at 20 μm on a periphery of the retina.

18. The lens apparatus of claim 15, wherein the first lens comprises a polymer lens with a kinoform surface having a quadratic blaze profile.

19. The lens apparatus of claim 15, wherein the shared housing includes a first geometric profile for coupling with the first lens and a second geometric profile for coupling with the second lens.

20. The lens apparatus of claim 15, wherein the shared housing is integrally formed with the second lens and includes a geometric profile for coupling with the first lens.

* * * * *